(12) United States Patent
Hsu (10) Patent No.: US 11,457,990 B2
(45) Date of Patent: Oct. 4, 2022

(54) DEVICES AND METHODS TO ENTRAP AEROSOLS AND DROPLETS

(71) Applicant: Ellen Hsu, Foster City, CA (US)

(72) Inventor: Ellen Hsu, Foster City, CA (US)

( * ) Notice: Subject to any disclaimer, the term of this patent is extended or adjusted under 35 U.S.C. 154(b) by 0 days.

(21) Appl. No.: 17/227,375

(22) Filed: Apr. 12, 2021

(65) Prior Publication Data
US 2021/0315654 A1 Oct. 14, 2021

Related U.S. Application Data

(60) Provisional application No. 63/100,986, filed on Apr. 11, 2020.

(51) Int. Cl.
*A61B 46/20* (2016.01)
*A61B 1/00* (2006.01)

(52) U.S. Cl.
CPC .............. *A61B 46/20* (2016.02); *A61B 1/00* (2013.01); *A61B 2046/205* (2016.02); *Y10T 442/2525* (2015.04)

(58) Field of Classification Search
None
See application file for complete search history.

(56) References Cited

U.S. PATENT DOCUMENTS

| | | | | |
|---|---|---|---|---|
| 4,553,968 A * | 11/1985 | Komis | ..................... | A61F 5/453 604/349 |
| 5,088,483 A * | 2/1992 | Heinecke | .............. | A61F 13/023 128/849 |
| 5,299,582 A * | 4/1994 | Potts | ....................... | A61F 13/00 128/846 |
| 5,305,765 A * | 4/1994 | Potts | ....................... | A61F 13/00 128/849 |
| 5,316,541 A * | 5/1994 | Fischer | ................ | A61G 10/005 128/849 |
| 5,680,653 A * | 10/1997 | Mathis | .................... | B32B 5/026 2/123 |
| 5,960,794 A | 10/1999 | Shaw | | |
| 6,235,659 B1 * | 5/2001 | McAmish | .......... | A41D 13/1209 2/114 |
| 6,267,115 B1 * | 7/2001 | Marshel | ................ | A61M 25/02 128/877 |
| 6,357,445 B1 * | 3/2002 | Shaw | ..................... | A61B 46/30 128/853 |
| 6,382,212 B1 * | 5/2002 | Borchard | ............... | A61B 46/00 128/849 |
| 7,100,213 B2 * | 9/2006 | Krautbauer | ............ | A41B 9/001 2/400 |

(Continued)

*Primary Examiner* — Arti Singh-Pandey
(74) *Attorney, Agent, or Firm* — Christopher Pilling (57) ABSTRACT

The invention encompasses devices and methods that at least partially entrap the droplets and aerosols from a person undergoing an aerosol/droplet-generating procedure, thereby reducing a health care worker's direct exposure to such health hazards. The device includes a planar cover structure impermeable to aerosols, droplets, fluids and gas. The planar cover structure providing a barrier between a health care worker and the body cavity or orifice of a patient. A hollow tubular extension forming an opening on the planar cover structure and the opening is configured to be positioned approximately on top of the body cavity or orifice of the patient. The opening configured to be reversibly closed via a closure mechanism.

5 Claims, 9 Drawing Sheets

(56) References Cited

U.S. PATENT DOCUMENTS

| | | | | |
|---|---|---|---|---|
| 7,299,803 B2* | 11/2007 | Kovac | A61B 42/20 | 128/849 |
| 7,343,919 B2* | 3/2008 | Czajka | A61B 46/20 | 128/849 |
| 7,543,587 B2* | 6/2009 | Yardan | A61B 46/20 | 128/849 |
| 10,874,150 B2* | 12/2020 | Stevenson | A41D 13/02 | |
| 2004/0199974 A1* | 10/2004 | Fancher | A61B 46/27 | 2/59 |
| 2006/0169290 A1* | 8/2006 | Harris | A61B 46/23 | 128/852 |
| 2007/0265586 A1* | 11/2007 | Joshi | A61F 13/0213 | 604/313 |
| 2008/0053462 A1* | 3/2008 | Teves | A61B 46/00 | 128/849 |
| 2009/0054847 A1* | 2/2009 | Bauss | A61M 5/3216 | 604/192 |
| 2012/0197206 A1* | 8/2012 | Glenn | A61M 25/02 | 604/180 |
| 2012/0222686 A1* | 9/2012 | Lockwood | A61B 90/04 | 128/849 |
| 2012/0247487 A1* | 10/2012 | Llinas | A61B 90/04 | 128/849 |
| 2013/0104910 A1* | 5/2013 | Kerner | A61B 46/00 | 128/853 |
| 2013/0247921 A1* | 9/2013 | Dye | A61B 46/00 | 128/853 |
| 2014/0007886 A1* | 1/2014 | Singh | A61B 46/30 | 128/854 |
| 2014/0163326 A1* | 6/2014 | Forsell | A61B 90/40 | 600/207 |
| 2014/0303541 A1* | 10/2014 | Vachon | A61F 13/00063 | 602/57 |
| 2015/0157774 A1* | 6/2015 | Zamierowski | A61M 1/90 | 604/319 |
| 2015/0159066 A1* | 6/2015 | Hartwell | A61F 13/0216 | 604/319 |
| 2018/0206708 A1* | 7/2018 | Miller | A61B 1/015 | |
| 2019/0038372 A1* | 2/2019 | Dine | A61B 46/30 | |
| 2020/0281686 A1* | 9/2020 | Finkelstein | A61B 90/30 | |
| 2020/0289334 A1* | 9/2020 | Choudhury | A61F 13/60 | |
| 2020/0375684 A1* | 12/2020 | Meah | A61B 46/30 | |
| 2021/0186128 A1* | 6/2021 | Gettman | A61B 46/30 | |
| 2021/0228069 A1* | 7/2021 | Matsumoto | A61B 1/00091 | |
| 2021/0290337 A1* | 9/2021 | Teodorescu | A61B 46/27 | |

* cited by examiner

DEVICES AND METHODS TO ENTRAP AEROSOLS AND DROPLETS

CROSS-REFERENCE TO RELATED APPLICATIONS

The present invention claims priority to provisional application Ser. No. 63/100,986, filed Apr. 11, 2020 entitled "Devices and Methods to Entrap Aerosols and Droplets" is hereby incorporated in its entirety at least by reference.

BACKGROUND OF THE INVENTION

1. Field of the Invention

The invention relates to devices and methods that at least partially entrap the droplets and aerosols from a person undergoing an aerosol/droplet-generating procedure, thereby reducing a health care worker's direct exposure to such health hazards.

2. Description of Related Art

Droplets and aerosols generated from certain medical procedures, including but not limited to those involving the oral cavity/airway/anus—such as laryngoscopy (performed in endotracheal intubation), bronchoscopy, EGD (esophago-gastro-duodenoscopy), colonoscopy, sigmoidoscopy, anoscopy, and dental procedures—have been shown to contain infectious, pathogenic materials such as bacteria, bacterial spores, and viral particles including SARS-CoV-2 causing the COVID-19 pandemic. Therefore, these droplets and aerosols are considered as potential health hazards to the health care worker performing an aerosol-generating procedure.

It would be beneficial to entrap these droplets and aerosols as much as possible during an aerosol-generating procedure to provide better protection to the health care worker performing the procedure. At the present time, there is no effective, simple method or device that allows significant reduction of direct exposure to the aerosols and droplets generated during the aerosol-generating procedure. Consequently, devices and methods to entrap aerosols and droplets are provided.

BRIEF SUMMARY OF THE INVENTION

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

It is one object of the present invention to reduce the direct exposure to the droplets and aerosols generated from a medical procedure involving a patient's oral cavity.

It is another object of the present invention to reduce the direct exposure to the droplets and aerosols generated from a medical procedure involving a patient's airway.

It is another object of the present invention to reduce the direct exposure to the droplets and aerosols generated from a procedure involving a body cavity or a body orifice of a person.

It is another object of the present invention to reduce the direct exposure to the droplets and aerosols generated from a procedure involving a body cavity or a body orifice of an animal.

It is yet another object of the present invention to provide devices that are simple and inexpensive to manufacture, that are simple to use, and that are robust in use.

In order to do so, in one aspect of the invention, a protective device for preventing direct exposure to the aerosols and droplets containing potentially infectious materials such as bacterial and viral particles including SARS-CoV-2 associated with COVID-19 generated during a medical or veterinary procedure involving a body cavity or orifice is provided, the protective device comprising a planar cover structure having a top surface and an undersurface, wherein the planar cover structure is impermeable to aerosols, droplets, fluids and gas, the planar cover structure providing a barrier between a health care worker and the body cavity or orifice of a patient; a hollow tubular extension forming an opening on the planar cover structure, wherein the hollow tubular extension is configured to be positioned approximately on top of the body cavity or orifice of the patient; and, the opening configured to be reversibly closed via a closure mechanism.

In one embodiment, the planar cover structure is deformable, pliable, and flexible. In one embodiment, the planar cover structure and the hollow tubular extension is partially transparent. In another embodiment, the planar cover structure is reversibly secured to a table or bed supporting the patient. In one embodiment, the planar cover structure is reversibly secured to the patient's body via an adhesive, an elastic band, or a fastener, such as a hook and loop fastener. In one embodiment, the opening of the hollow tubular extension allows passage of a medical device. In another embodiment, the medical device is an endoscope. In yet another embodiment, the closure mechanism is a cord, an elastic band, a valve, a zipper, a fastener, a drawstring, a diaphragm, an elastic membrane, a sponge, or foam.

In another aspect of the invention, a protective device for preventing direct exposure to the aerosols and droplets containing potentially infectious materials such as bacterial and viral particles including SARS-CoV-2 associated with COVID-19 generated during a medical or veterinary procedure involving a body cavity or orifice is provided, the protective device comprising a planar cover structure having a top surface and an undersurface, wherein the planar cover structure is impermeable to aerosols, droplets, fluids and gas, the planar cover structure providing a barrier between a health care worker and the body cavity or orifice of a patient; an opening on the planar cover structure, wherein opening is configured to be positioned approximately on top of the body cavity or orifice of the patient; and, the opening configured to be reversibly closed, wherein the opening is an elastic membrane barrier having a varying sized opening.

In yet another aspect of the invention, a method of preventing direct exposure to the aerosols and droplets during a medical procedure involving a body cavity or orifice of a patient is provided, the method comprising steps: (a) providing a protective barrier device comprising a planar cover structure and an opening on the planar cover structure, wherein the opening is configured to be reversibly closed; (b) reversibly securing the planar cover structure in the vicinity of the body cavity or orifice, with the opening positioned in the vicinity of the body cavity or orifice; (c) placement of a medical device through the opening and into the opening of the body cavity or orifice; (d) closing the opening around the medical device; and, (e) initiation and completion of the medical procedure generating the aerosols and droplets with the protective barrier device in place.

The foregoing has outlined rather broadly the more pertinent and important features of the present disclosure so that the detailed description of the invention that follows may be better understood and so that the present contribution to the art can be more fully appreciated. Additional features of the invention will be described hereinafter which form the subject of the claims of the invention. It should be appreciated by those skilled in the art that the conception and the disclosed specific methods and structures may be readily utilized as a basis for modifying or designing other structures for carrying out the same purposes of the present disclosure. It should be realized by those skilled in the art that such equivalent structures do not depart from the spirit and scope of the invention as set forth in the appended claims.

BRIEF DESCRIPTION OF THE SEVERAL VIEWS OF THE DRAWINGS

Other features and advantages of the present invention will become apparent when the following detailed description is read in conjunction with the accompanying drawings, in which:

FIG. 1A illustrates the top view of one embodiment of the present invention, including cover or cover body (1), cover attachment means (2), and cover opening (3).

FIG. 1B illustrates the side view of the cover of the present invention, including cover body (1), and cover opening (3).

FIG. 2A illustrates the 3-dimensional view of one variation of the cover opening of the present invention, showing cover body (1), cover opening (3), cover sleeve (4), cord (5), and cord lock (6).

FIG. 2B illustrates the same embodiment illustrated in FIG. 2A, showing cover body (1), cover opening (3), cover sleeve (4), cord (5), and cord lock (6).

FIG. 2C is a cross-sectional view of the embodiment illustrated in FIG. 2A, showing cover body (1), cover opening (3), cover sleeve (4), and cord (5).

FIG. 2D is a cross-sectional view of the embodiment illustrated in FIG. 2B, showing cover body (1), cover opening (3), cover sleeve (4), and cord (5).

FIGS. 2E1-2E3 illustrate a method of using the present invention during an endoscopic procedure.

FIG. 3A illustrates the 3-dimensional view of one variation of the cover opening of the present invention, showing cover body (1), cover opening (3), cover sleeve (4), and elastic band/cord (8).

FIG. 3B illustrates the same embodiment illustrated in FIG. 3A, showing cover body (1), cover opening (3), cover sleeve (4), and elastic band/cord (8).

FIG. 3C is a cross-sectional view of the embodiment illustrated in FIG. 3A, showing cover body (1), cover opening (3), cover sleeve (4), and elastic band/cord (8).

FIG. 3D is a cross-sectional view of the embodiment illustrated in FIG. 3B, showing cover body (1), cover opening (3), cover sleeve (4), elastic band/cord (8).

FIGS. 3E1-3E3 illustrate a method of using the present invention during an endoscopic procedure.

FIG. 4A illustrates the 3-dimensional view of one variation of the cover opening of the present invention, showing cover body (1), cover opening (3), cover sleeve (4), elastic membrane barrier (9) with its small opening (10).

FIGS. 4B1-4B3 illustrate a method of using the present invention during an endoscopic procedure.

FIG. 4C1-4C3 illustrate another embodiment of the present invention.

FIG. 5A is a cross-sectional view of an embodiment of the invention, showing cover body (1), cover opening (3), and cord (5).

FIG. 5B is a cross-sectional view of the embodiment illustrated in FIG. 5A, showing cover body (1), cover opening (3), and cord (5).

FIG. 6A is a cross-sectional view of an embodiment of the invention, showing cover body (1), cover opening (3), and elastic band/cord (8).

FIG. 6B is a cross-sectional view of the embodiment illustrated in FIG. 6A, showing cover body (1), cover opening (3), and elastic band/cord (8).

FIG. 7A is a cross-sectional view of an embodiment of the invention, showing cover body (1), cover opening (3), elastic membrane barrier (9) with its small opening (10).

FIG. 7B is a cross-sectional view of the embodiment illustrated in FIG. 7A, showing cover body (1), cover opening (3), elastic membrane barrier (9) with its small opening (10), and endoscope distal end (7).

FIG. 8 illustrates the top view of another embodiment of the present invention, showing cover or cover body (1), cover attachment means (2), cover opening (3), and additional cover opening (11).

FIG. 9 illustrates the 3-dimensional view of another embodiment of the present invention, showing cover body (12), cover opening (3), cover opening for torso (13), and cover opening for extremity (14).

FIG. 10A illustrates the top view of another embodiment of the present invention, showing cover or cover body (1), cover attachment means (2), and cover opening (3).

FIG. 10B illustrates the 3-dimensional view of the same embodiment of the invention illustrated in FIG. 10A, showing cover or cover body (1), cover attachment means (2), and cover opening (3).

DETAILED DESCRIPTION OF EMBODIMENTS OF THE INVENTION

The following description is provided to enable any person skilled in the art to make and use the invention and sets forth the best modes contemplated by the inventor of carrying out his invention. Various modifications, however, will remain readily apparent to those skilled in the art, since the general principles of the present invention have been defined herein to specifically provide devices and methods to entrap aerosols and droplets.

FIG. 1A illustrates the top view of one embodiment of the present invention, including cover or cover body (1), cover attachment means (2), and cover opening (3). The cover (1) is a flat, planar structure that has 2 surfaces—an undersurface that comes in physical contact with the patient undergoing the medical procedure, and a top surface that comes in contact with the hands of the health care provider performing the medical procedure. The cover (1) may be of any material composition/shape/design/dimensions, and it may be transparent or opaque. In certain embodiments, a flexible, thin, transparent cover is preferred, providing better visualization of the body landmarks under the cover to the health care provider performing the medical procedure. At least part of the edge of the cover (1) and/or the cover opening (3) is at least partially coupled with an adhesive, a cord/string, a hook and loop fastener (such as Velcro), an elastic band/cord, and/or a layer of foam/sponge in certain embodiments of the invention (not illustrated in the current figure). The attachment means (2) of the cover may be of any design/ material composition/dimensions/number. In the present figure, straps such as Velcro straps are associated with the corners of the cover, and these straps can be used to reversibly secure the cover to the patient, another part of the cover body (1), and/or the hospital bed/gurney/operating table etc that support the patient undergoing the aerosol-generating medical procedure. In certain embodiments of the cover of the invention, adhesives (such as those commonly used in surgical drapes) are integrated as part of the cover undersurface that comes in contact with the patient, allowing better reversible attachment of the cover to the patient. In certain embodiments of the invention, the cover attachment means (2) is absent—in which case, the use of adhesives (as part of the cover undersurface that comes in contact with the patient) may or may not be present. The cover opening or hollow tubular extension (3) may be of any design/dimensions/material composition/number. In certain embodiments of the invention, it is located in the center of the cover (1), as shown in the present figure. However, its location may vary in other embodiments of the invention (not illustrated). The cover is preferably impermeable to aerosols, droplets, fluids and gas. The cover is preferably deformable, pliable, and flexible.

Figure 1A:
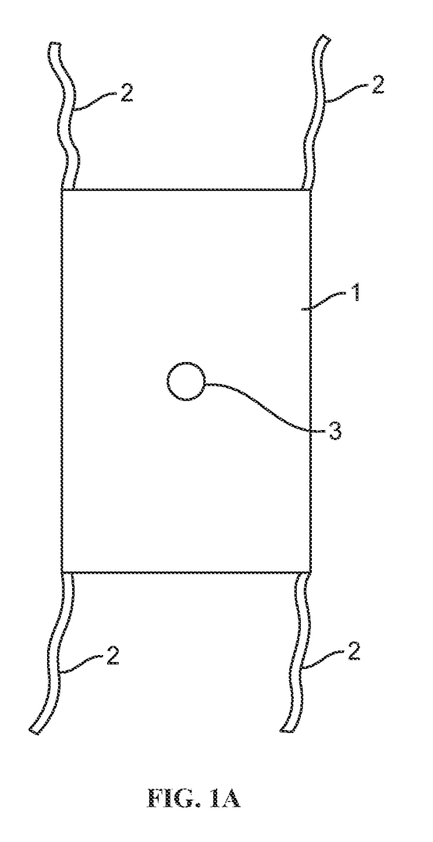
Figure 1B:
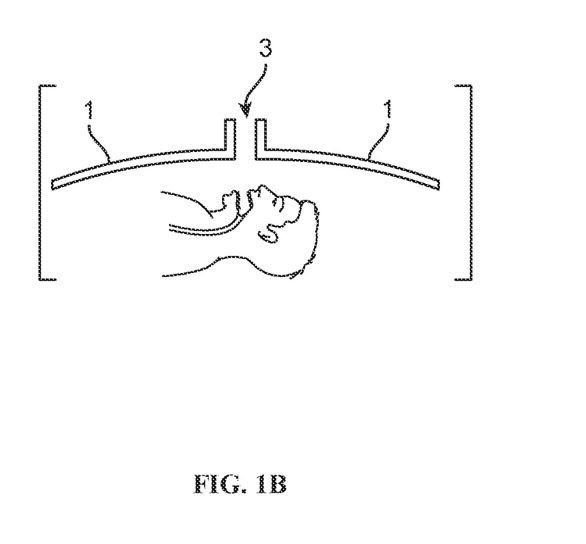

FIG. 1B illustrates the side view of the cover of the present invention, including cover body (1), cover opening (3). The cover opening (3) is positioned appropriately on top of the target patient body cavity, which was the oral cavity in the present figure, during the medical procedure. The cover (1) serves as a barrier to reduce the exposure of the health care worker performing the medical procedure to the aerosols and droplets coming from the patient's oral cavity during the medical procedure.

Figure 2A:
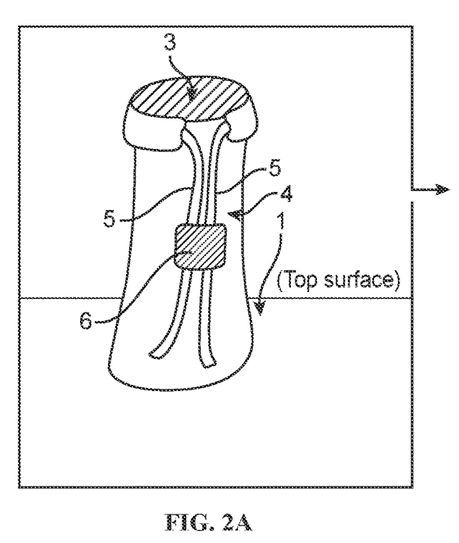

FIG. 2A illustrates the 3-dimensional view of one variation of the cover opening of the present invention, showing cover body (1), cover opening (3), cover sleeve (4), cord (5), and cord lock (6). The cover sleeve (4) associated with the cover body (1) has a hollow lumen that communicates with the cover opening (3) and protrudes/extends from the top surface of the cover (the side/surface that does not come in contact with the patient). The hollow lumen of the cover sleeve (4) and the cover opening (3) allows the passage of a medical device such as an endoscope used in medical endoscopy. The cord (5) is associated with the terminal end (top end) of the cover sleeve (4) (the end of the cover sleeve that is away from the cover body). In one embodiment, the terminal end of the cover sleeve (4) is circumferentially surrounded by the cord (5), as shown in the present figure. The noose created by the cord (5) can be loosened or tightened reversibly by sliding the cord lock (6) toward or away from the 2 tail ends of the cord (5), respectively. In the present figure, the cover opening (3) is open, as the cord lock (6) is close to the tail ends of the cord (5) and away from the cover opening (3). The cord sleeve (4), cord (5), and cord lock (6) may be of any dimensions/design/material composition. In certain embodiments, the cord may or may not be elastic in nature.

Figure 2B:
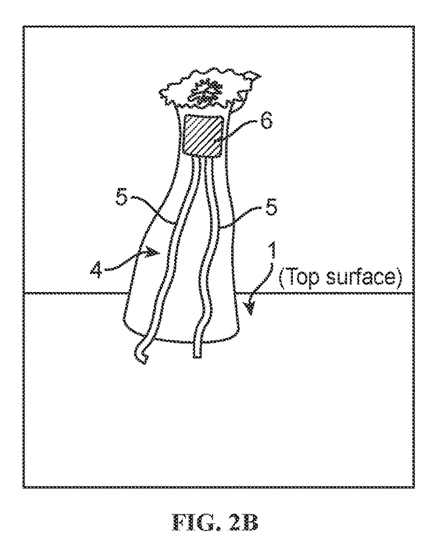

FIG. 2B illustrates the same embodiment illustrated in FIG. 2A, showing cover body (1), cover opening (3), cover sleeve (4), cord (5), and cord lock (6). In the present figure, the cord lock (6) is slid away from its tail ends, thereby securely and reversibly closing the cover opening (3) near the terminal end of the cover sleeve (4).

Figure 2C:
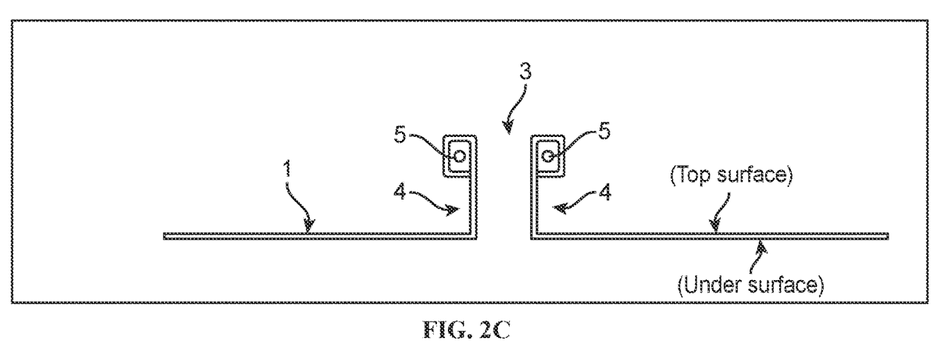

FIG. 2C is a cross-sectional view of the embodiment illustrated in FIG. 2A, showing cover body (1), cover opening (3), cover sleeve (4), cord (5). In this drawing, the cover opening (3) is open, allowing passage of a medical device such as an endoscope.

Figure 2D:
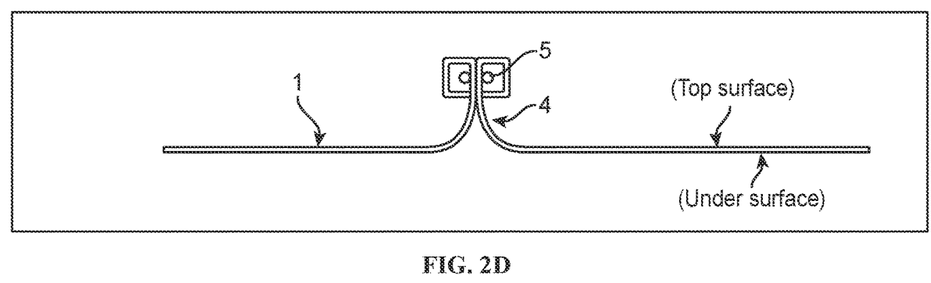
Figure 2E:
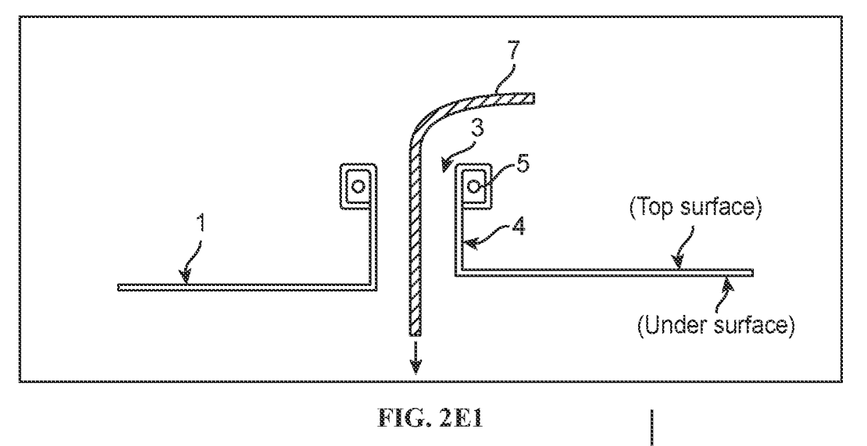
Figure 2E:
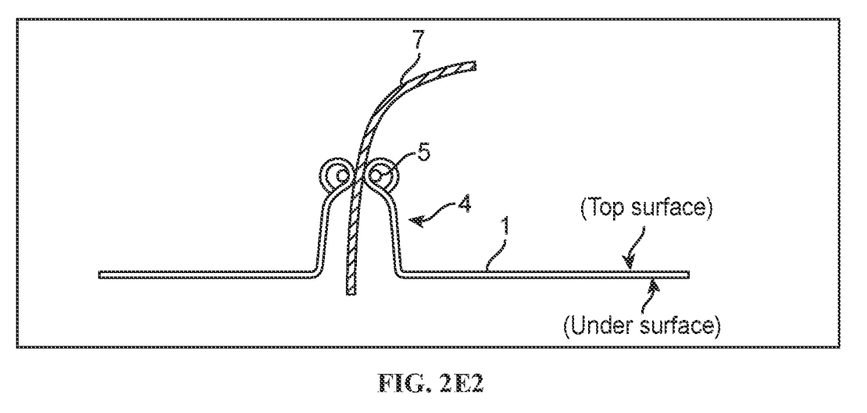
Figure 2E:
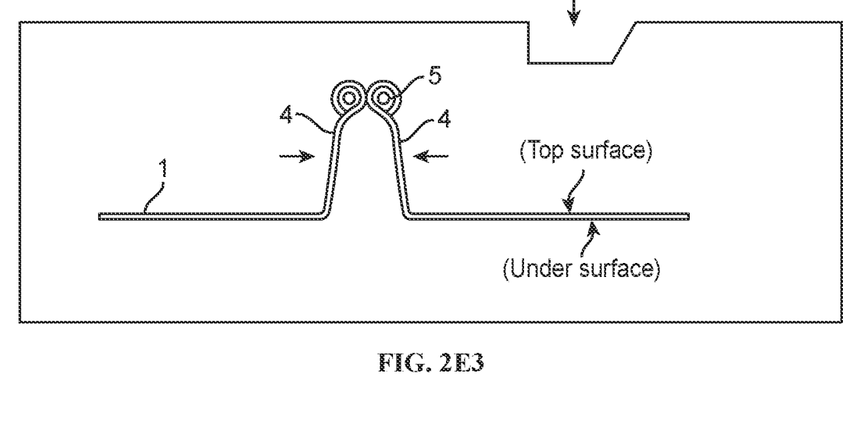

FIG. 2D is a cross-sectional view of the embodiment illustrated in FIG. 2B, showing cover body (1), cover opening (3), cover sleeve (4), cord (5). In this drawing, the cover opening (3) is closed. With its cover opening (3) in the closed position, the cover (1) serves a shield preventing (or at least reducing) aerosols/droplets emanating from the patient body cavity from reaching the health care provider performing the medical procedure.

FIG. 2E illustrates a method of using the present invention during an endoscopic procedure. FIG. 2E1 is a cross-sectional view of the embodiment illustrated in FIG. 2A-B, showing cover body (1), cover opening (3), cover sleeve (4), cord (5), and distal portion (tip end) of an endoscope (7). In this drawing, the cover opening (3) is open, allowing free passage of a medical device such as an endoscope through the lumen of the cover sleeve (4) into the target body cavity of the patient (not illustrated). FIG. 2E2 is a cross-sectional view of the embodiment illustrated in FIG. 2A-B, showing cover body (1), cover opening (3), cover sleeve (4), cord (5), and distal portion (tip end) of an endoscope (7). In this drawing, the cover opening (3) is closed around the endoscope (by sliding the cord lock towards the cord sleeve opening), thereby preventing aerosols/droplets (emanating from the target patient body cavity) from traveling through the cover opening to reach the health care provider performing the medical procedure. FIG. 2E3 is a cross-sectional view of the embodiment illustrated in FIG. 2A-B, showing cover body (1), cover opening (3), cover sleeve (4), cord (5). In this drawing, the cover opening (3) remains closed after the removal of the endoscope from the patient body cavity (at the conclusion of the medical procedure), thereby preventing aerosols/droplets (emanating from the target patient body cavity) from traveling through the cover opening to reach the health care provider performing the medical procedure. In addition to the closure mechanism exemplified by the cord/cord lock in the present figure, the health care provider can also manually compress (choke off) the cover sleeve (4)—see small arrows in the figure—thereby augmenting the closure of the cover opening (3) at the conclusion of the medical procedure. Note that the cord lock can be manually slid away from the cord sleeve (4), thereby achieving reopening of the cover opening (3). Note that the application of lubricant to the cover opening (3) may facilitate the passage of the endoscope (not illustrated).

Figure 3A:
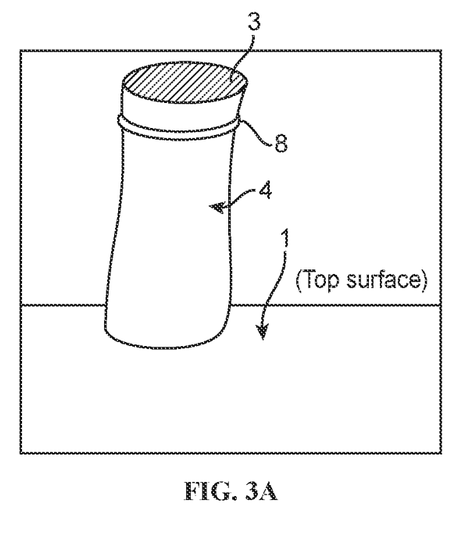

FIG. 3A illustrates the 3-dimensional view of one variation of the cover opening of the present invention, showing cover body (1), cover opening (3), cover sleeve (4), elastic band/cord (8). The cover sleeve (4) associated with the cover body (1) has a hollow lumen that communicates with the cover opening (3) and protrudes/extends from the top surface of the cover (the side/surface that does not come in contact with the patient). The hollow lumen of the cover sleeve (4) and the cover opening (3) allows the passage of a medical device such as an endoscope used in medical endoscopy. An elastic cord/band (8) is associated with the terminal end (top end) of the cover sleeve (4) (the end of the cover sleeve that is away from the cover body). In one embodiment, the terminal end of the cover sleeve (4) is circumferentially surrounded by the elastic cord (8), as shown in the present figure. The cord sleeve (4), cord (8) may be of any dimensions/design/material composition. In the present figure, the elastic cord/band (8) is manually stretched open, displaying the open cover opening (3).

Figure 3B:
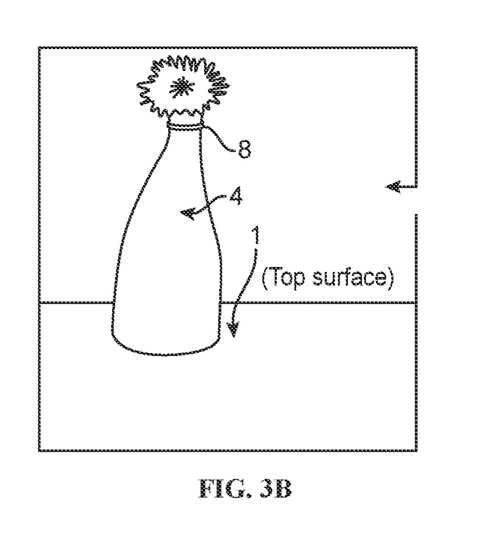

FIG. 3B illustrates the same embodiment illustrated in FIG. 3A, showing cover body (1), cover opening (3), cover sleeve (4), elastic band/cord (8). In the present figure, the elastic band/cord is relaxed in its native/natural state, thereby securely and reversibly closing the cover opening (3) near the terminal end of the cover sleeve (4).

Figure 3C:
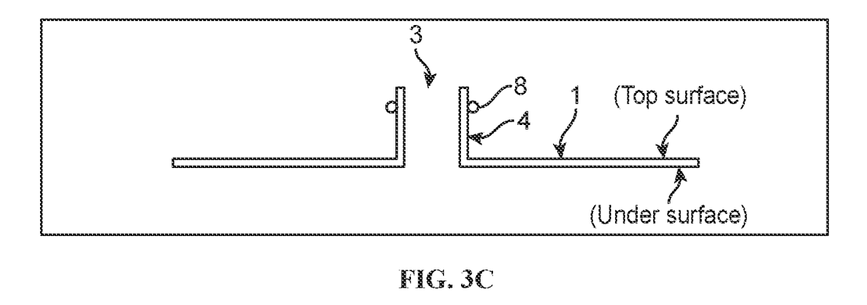

FIG. 3C is a cross-sectional view of the embodiment illustrated in FIG. 3A, showing cover body (1), cover opening (3), cover sleeve (4), elastic band/cord (8). In this drawing, the cover opening (3) is open (by manually stretching opening the elastic cord/band (8)), allowing passage of a medical device such as an endoscope.

Figure 3D:
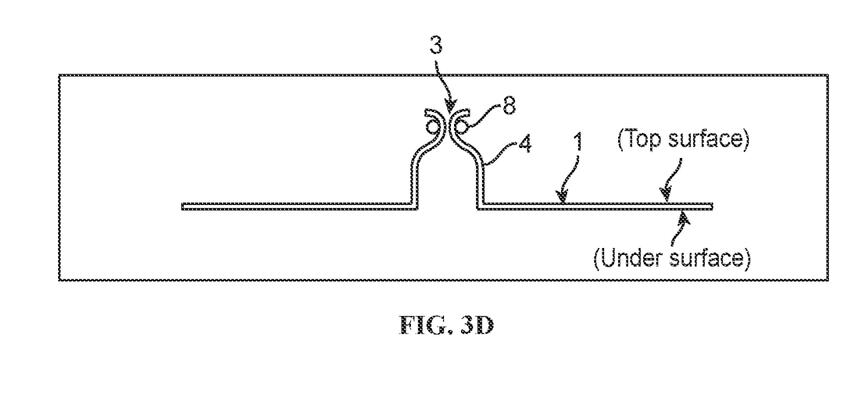
Figure 3E:
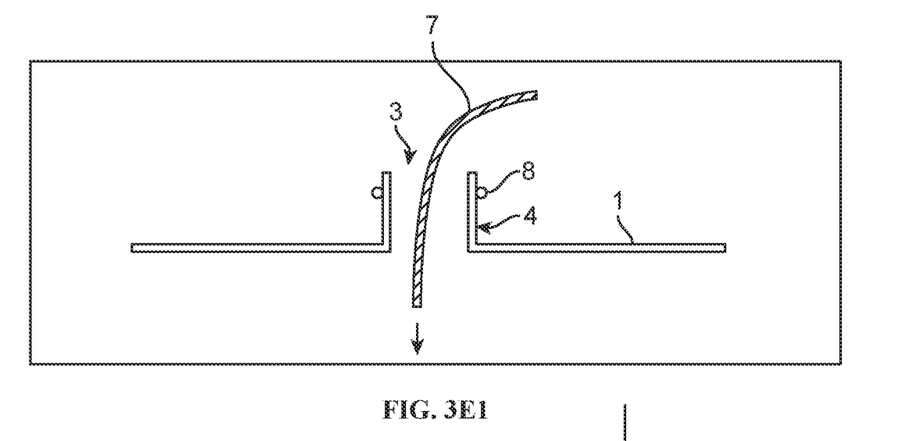
Figure 3E:
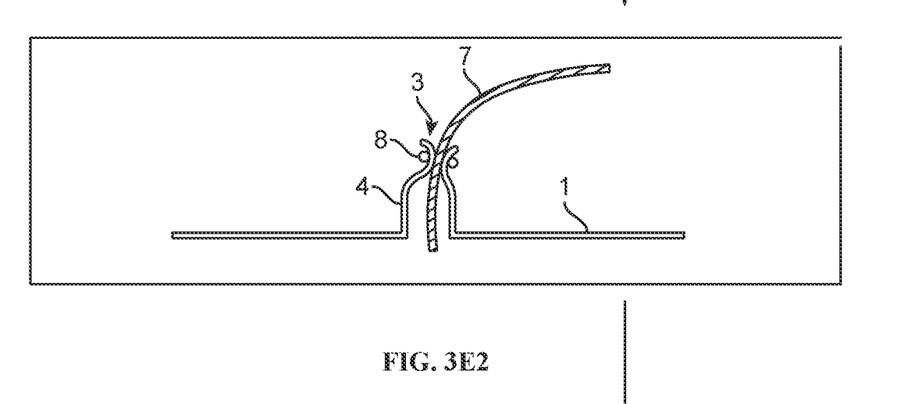
Figure 3E:
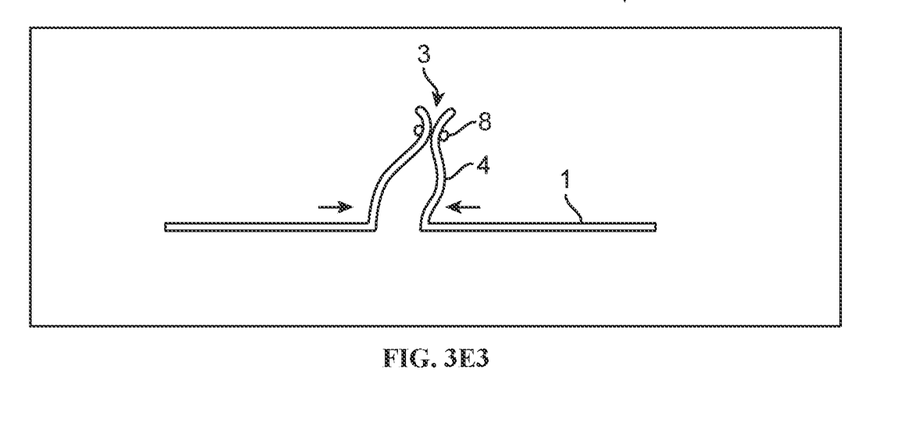

FIG. 3D is a cross-sectional view of the embodiment illustrated in FIG. 3B, showing cover body (1), cover opening (3), cover sleeve (4), elastic band/cord (8). In this drawing, the cover opening (3) is closed, as the elastic cord/band (8) is in its natural, relaxed state. With its cover opening (3) in the closed position, the cover (1) serves a shield preventing (or at least reducing) aerosols/droplets emanating from the patient body cavity from reaching the health care provider performing the medical procedure.

FIG. 3E illustrates a method of using the present invention during an endoscopic procedure. FIG. 3E1 is a cross-sectional view of the embodiment illustrated in FIG. 3A-B, showing cover body (1), cover opening (3), cover sleeve (4), elastic band/cord (8), and distal portion (tip end) of an endoscope (7). In this drawing, the cover opening (3) is manually stretched open, allowing free passage of a medical device such as an endoscope through the lumen of the cover sleeve (4) into the target body cavity of the patient (not illustrated). FIG. 3E2 is a cross-sectional view of the embodiment illustrated in FIG. 3A-B, showing cover body (1), cover opening (3), cover sleeve (4), elastic band/cord (8), and distal portion (tip end) of an endoscope (7). In this drawing, the cover opening (3) is closed around the endoscope (by allowing the elastic cord/band to return to its natural, relaxed state), thereby preventing aerosols/droplets (emanating from the target patient body cavity) from traveling through the cover opening to reach the health care provider performing the medical procedure. FIG. 3E3 is a cross-sectional view of the embodiment illustrated in FIG. 3A-B, showing cover body (1), cover opening (3), cover sleeve (4), elastic band/cord (8). In this drawing, the cover opening (3) remains closed after the removal of the endoscope from the patient body cavity (at the conclusion of the medical procedure), thereby preventing aerosols/droplets (emanating from the target patient body cavity) from traveling through the cover opening to reach the health care provider performing the medical procedure. In addition to the closure mechanism exemplified by the elastic cord/band in the present figure, the health care provider can also manually compress (choke off) the cover sleeve (4)—see small arrows in the figure—thereby augmenting the closure of the cover opening (3) at the conclusion of the medical procedure. Note that the application of lubricant to the cover opening (3) may facilitate the passage of the endoscope (not illustrated).

Figure 4A:
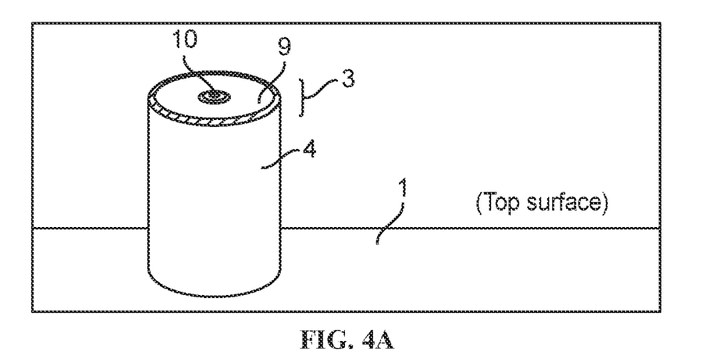
Figure 4B:
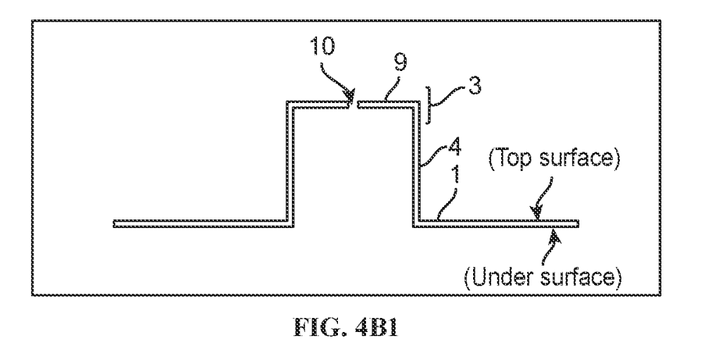
Figure 4B:
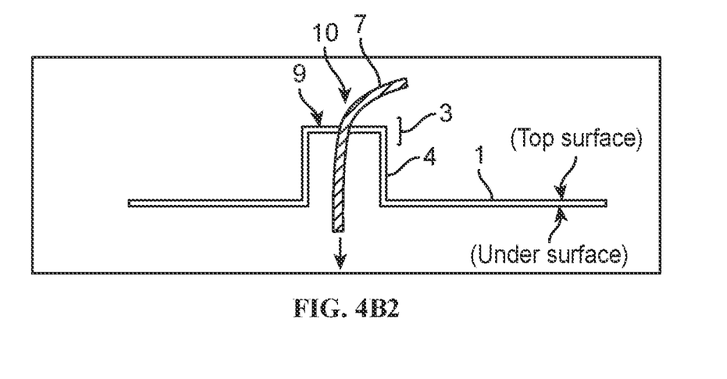
Figure 4B:
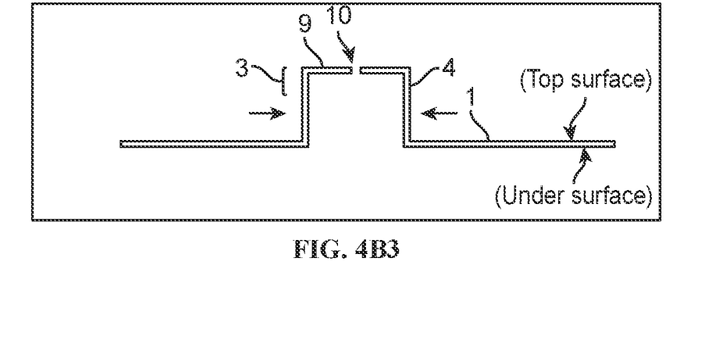
Figure 4C:
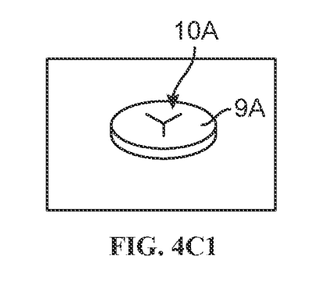
Figure 4C:
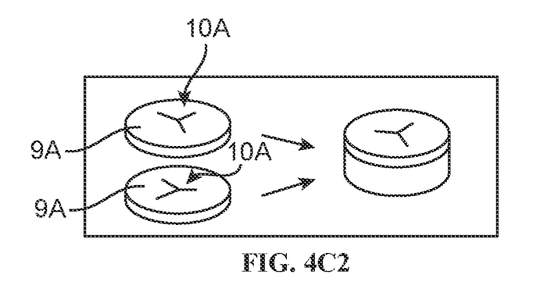
Figure 4C:
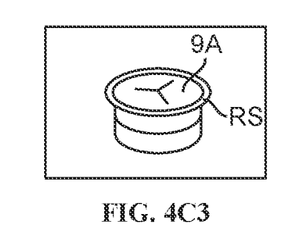

FIG. 4A illustrates the 3-dimensional view of one variation of the cover opening of the present invention, showing cover body (1), cover opening (3), cover sleeve (4), elastic membrane barrier (9) with its small opening (10). The cover sleeve (4) associated with the cover body (1) has a hollow lumen that communicates with the cover opening (3) and protrudes/extends from the top surface of the cover (the side/surface that does not come in contact with the patient). The hollow lumen of the cover sleeve (4) and the cover opening (3) allows the passage of a medical device such as an endoscope used in medical endoscopy. An elastic membrane barrier (9) with its small opening (10) is associated with the terminal end (top end) of the cover sleeve (4) (the end of the cover sleeve that is away from the cover body).

The membrane barrier (9) has a small opening (10) in its natural, relaxed state, as shown in the present figure. The membrane barrier (9) is preferably elastic/stretchable, thereby allowing its opening (10) to increase in diameter to accommodate the passage of a medical device such as an endoscope. The cord sleeve (4), membrane barrier (9) and its small opening (10) may be of any dimensions/design/material composition.

FIG. 4B illustrates a method of using the present invention during an endoscopic procedure. FIG. 4B1 is a cross-sectional view of the embodiment illustrated in FIG. 4A, showing cover body (1), cover opening (3), cover sleeve (4), elastic membrane barrier (9) with its small opening (10). FIG. 4B2 is a cross-sectional view of the embodiment illustrated in FIG. 4A, showing cover body (1), cover opening (3), cover sleeve (4), elastic membrane barrier (9) with its small opening (10), and endoscope distal end (7). In this drawing, the endoscope (7) is passed through the cover opening (3) via the small opening (10) of the elastic membrane barrier (9), through lumen of the cover sleeve (4), and into the target patient body cavity (not illustrated). Note that the cover opening (3) with its elastic membrane (9) is closed around the endoscope (as the small opening (10) of the elastic membrane barrier is stretched to a larger diameter to accommodate the exterior of the endoscope), thereby preventing aerosols/droplets (emanating from the target patient body cavity) from traveling through the cover opening to reach the health care provider performing the medical procedure. FIG. 4B3 is a cross-sectional view of the embodiment illustrated in FIG. 4A, showing cover body (1), cover opening (3), cover sleeve (4), elastic membrane barrier (9) with its small opening (10). In this drawing, the cover opening (3) remains closed after the removal of the endoscope from the patient body cavity (at the conclusion of the medical procedure), thereby preventing aerosols/droplets (emanating from the target patient body cavity) from traveling through the cover opening to reach the health care provider performing the medical procedure. In addition to the closure mechanism exemplified by the elastic cord/band in the present figure, the health care provider can also manually compress (choke off) the cover sleeve (4)—see small arrows in the figure—thereby augmenting the closure of the cover opening (3) at the conclusion of the medical procedure. Note that the application of lubricant to the cover opening (3) and/or elastic membrane barrier (9) with a small opening (10) may facilitate the passage of the endoscope (not illustrated).

FIG. 4C illustrates another embodiment of the present invention similar to the embodiment described in FIGS. 4A-B, in which the elastic membrane barrier (9) illustrated in FIGS. 4A-B is in the form of 1 or more layers of flexible foam/sponge (9A) with at least one opening (10A). FIG. 4C1 shows a 3-dimensional view of the single-layer sponge/foam (9A) with at least 1 opening (10A) that allows passage of an endoscope. FIG. 4C2 shows a 3-dimensional view of the combination of 2 layers of sponge/foam (9A) with elongated openings of different orientations (10A), which allow the passage of an endoscope. In this figure, overlapping the slit openings of different orientations of the sponges allow better co-aptation of the sponges around the endoscope and minimize the potential space/gap between the sponge and the endoscope during endoscope passage. The sponge/foam may be of any dimensions/design, and it may be at least partially supported by or associated with a rigid structure. FIG. 4C3 illustrates one example of such rigid structure (RS), which is rigid ring/frame surrounding the periphery of the sponge (9A). Such structure (RS) allows easier passage of the endoscope through the opening(s) of the sponge(s) during device deployment.

Figure 5A:
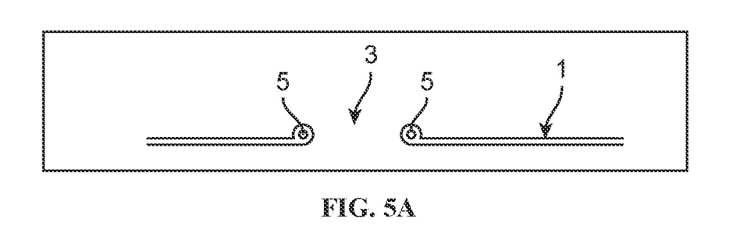

FIG. 5A is a cross-sectional view of an embodiment of the invention, showing cover body (1), cover opening (3), and cord (5). In this embodiment, there is no cover sleeve (such as that shown in the embodiments illustrated in FIG. 2), and the cord (5) is coplanar with the cover surface (1). In this drawing, the cover opening (3) is open, allowing passage of a medical device such as an endoscope. The cord (5) is circumferentially associated with the cover opening (3). The noose created by the cord (5) can be loosened or tightened reversibly by sliding the cord lock (as shown in FIG. 2; not illustrated here) toward or away from the 2 tail ends of the cord (5), respectively. In the present figure, the cover opening (3) is open, as the cord lock (not illustrated) is close to the tail ends of the cord (5) and away from the cover opening (3). The cord (5) and cord lock (not illustrated) may be of any dimensions/design/material composition. In certain embodiments, the cord may or may not be elastic in nature.

Figure 5B:
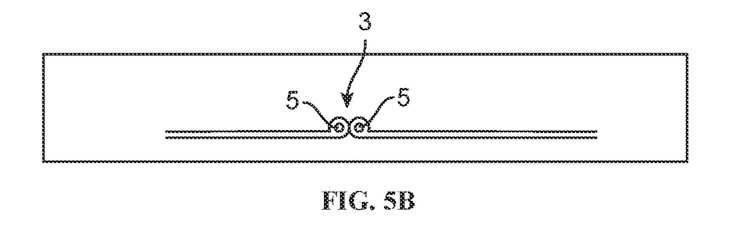

FIG. 5B is a cross-sectional view of the embodiment illustrated in FIG. 5A, showing cover body (1), cover opening (3), and cord (5). In this drawing, the cover opening (3) is closed, as the cord lock (not illustrated) is moved towards the cover opening (3) to close the noose opening. With its cover opening (3) in the closed position (with or without a medical device passing through its opening), the cover (1) serves a shield preventing (or at least reducing) aerosols/droplets emanating from the patient body cavity from reaching the health care provider performing the medical procedure.

Figure 6A:
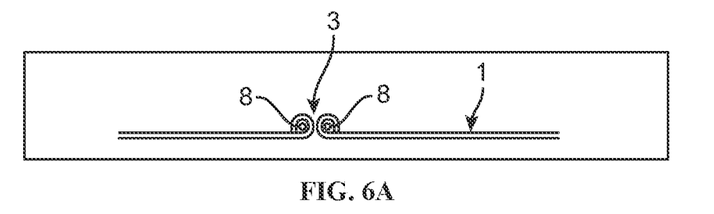

FIG. 6A is a cross-sectional view of an embodiment of the invention, showing cover body (1), cover opening (3), elastic band/cord (8). In this embodiment, there is no cover sleeve (such as that shown in the embodiments illustrated in FIG. 3), and the elastic band/cord (8) is co-planar with the cover surface (1). In this drawing, the cover opening (3) is open (by manually stretching opening the elastic cord/band (8)), allowing passage of a medical device such as an endoscope. The cover opening (3) is circumferentially surrounded by the elastic cord (8), as shown in the present figure. The cord (8) may be of any dimensions/design/material composition. In the present figure, the elastic cord/band (8) is manually stretched open, displaying the open cover opening (3).

Figure 6B:
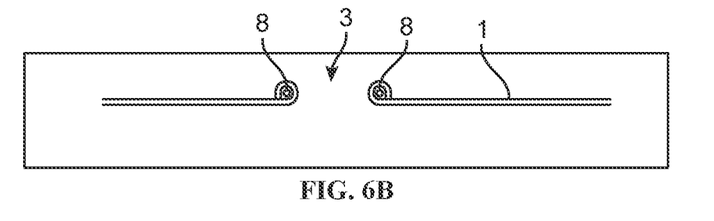

FIG. 6B is a cross-sectional view of the embodiment illustrated in FIG. 6A, showing cover body (1), cover opening (3), elastic band/cord (8). In this drawing, the cover opening (3) is closed, as the elastic cord/band (8) is in its natural, relaxed state. With its cover opening (3) in the closed position (with or without a medical device passing through its opening), the cover (1) serves a shield preventing (or at least reducing) aerosols/droplets emanating from the patient body cavity from reaching the health care provider performing the medical procedure.

Figure 7A:
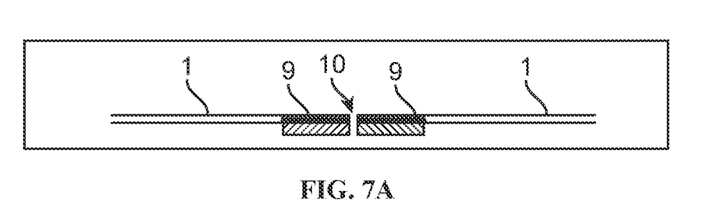

FIG. 7A is a cross-sectional view of an embodiment of the invention, showing cover body (1), cover opening (3), elastic membrane barrier (9) with its small opening (10). In this embodiment, there is no cover sleeve (such as that shown in the embodiments illustrated in FIG. 4), and the elastic membrane barrier (9) is coupled with the cover surface (1). An elastic membrane barrier (9) with its small opening (10) is associated with the cover opening (3). The membrane barrier (9) has a small opening (10) in its natural, relaxed state, as shown in the present figure. The membrane barrier (9) is preferably elastic/stretchable, thereby allowing its opening (10) to increase in diameter to accommodate the passage of a medical device such as an endoscope. The membrane barrier (9) and its small opening (10) may be of any dimensions/design/material composition. In certain embodiments of the invention, the elastic membrane barrier (9) involves at least 1 layer of sponge/foam (preferably stretchable and flexible) with at least 1 opening that allows passage of an endoscope. Examples of such foam/sponge design were described in FIG. 4C earlier, including the combination of 2 or more layers of sponge with elongated openings of different orientations. Such foam/sponge design/element may be coupled with (or integrated into) a bite block (also known as a mouth guard or a mouthpiece used to protect the mouth and the endoscope) commonly used during upper GI endoscopy/esophagogastroduodenoscopy (EGD) and bronchoscopy.

Figure 7B:
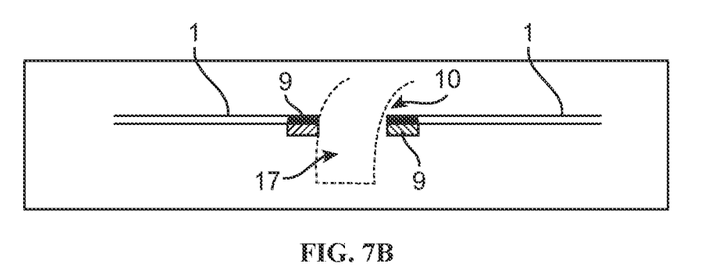

FIG. 7B is a cross-sectional view of the embodiment illustrated in FIG. 7A, showing cover body (1), cover opening (3), elastic membrane barrier (9) with its small opening (10), and endoscope distal end (7). In this drawing, the endoscope (7) is passed through the cover opening (3) via the small opening (10) of the elastic membrane barrier (9) and into the target patient body cavity (not illustrated). Note that the cover opening (3) with its elastic membrane (9) is closed around the endoscope (as the small opening (10) of the elastic membrane barrier is stretched to a larger diameter to accommodate the exterior of the endoscope), thereby preventing aerosols/droplets (emanating from the target patient body cavity) from traveling through the cover opening to reach the health care provider performing the medical procedure. In certain embodiments of the invention, the elastic membrane barrier (9) involves at least 1 layer of sponge/foam (preferably stretchable and flexible) with at least 1 opening that allows passage of an endoscope. Examples of such foam/sponge design were described in FIG. 4C earlier, including the combination of 2 or more layers of sponge with elongated openings of different orientations. Such foam/sponge design/element may be coupled with (or integrated into) a bite block (also known as a mouth guard or a mouthpiece used to protect the mouth and the endoscope) commonly used during upper GI endoscopy/esophagogastroduodenoscopy (EGD) and bronchoscopy.

Figure 8:
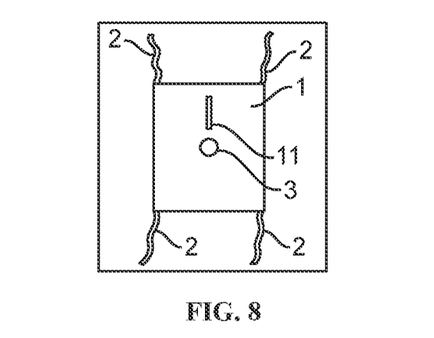

FIG. 8 illustrates the top view of another embodiment of the present invention, showing cover or cover body (1), cover attachment means (2), cover opening (3), and additional cover opening (11). The details of the cover body (1), cover attachment means (2), and cover opening (3) have been described in previous figures (FIGS. 1-7). The additional cover opening (11) may be of any number/dimensions/design/shape/location/orientation, and it is preferably reversibly closable via any mechanism. One example is a linear opening that is lined with a zipper-which allows reversible opening and closure of the linear opening via a zipper mechanism. Another method of reversible opening and closing of such additional cover opening (11) may involve the use of a hook-and-loop fastener such as a Velcro mechanism or a magnet (with or without a cover flap). Such additional opening (11) provides an extra access to the airways by the anesthesia team/provider during an endoscopy in the vicinity of the airways. In certain embodiments of the present invention, such additional cover opening (11) may be greater than 1 in number.

Figure 9:
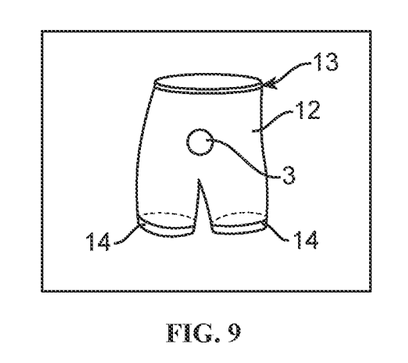

FIG. 9 illustrates the 3-dimensional view of another embodiment of the present invention, showing cover body (12), cover opening (3), cover opening for torso (13), and cover opening for extremity (14). The details of the cover opening (3) have been described in previous figures (See FIGS. 1-7). The cover body (12) may be of any material composition/shape/design/dimensions/configuration, and it may be transparent or opaque. In certain embodiments, a flexible, thin, transparent cover is preferred, providing better visualization of the body landmarks under the cover to the health care provider performing the medical procedure. In certain embodiments, the cover body (12) has an upper opening to accommodate the torso/waist/abdomen of the patient (13) and 2 lower openings to accommodate the lower extremities/groins of the patient (14)—in fact, the cover body (12) may have the configuration of shorts/underwear/diapers, as shown in the figure. The upper and lower openings (13, 14) of the cover body (12) are reversibly closable and/or elasticized (via any mechanism/design such as use of elastic band, tourniquet/string, etc.)—so that the interior space of the cover body (12) does not communicate with the environment outside the cover body (12), thereby preventing aerosol/droplet emanating from the target body orifice (anus/colon) from disseminating outside the cover body (12) during the endoscopy procedure (lower GI endoscopy such as colonoscopy and sigmoidoscopy).

Figure 10A:
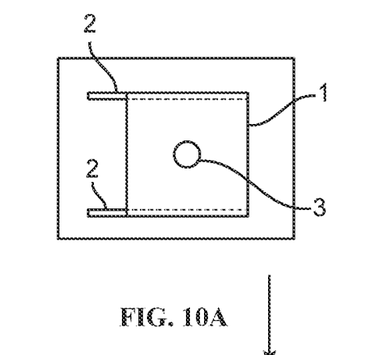

FIG. 10A illustrates the top view of another embodiment of the present invention, showing cover or cover body (1), cover attachment means (2), and cover opening (3). The details of the cover body (1), cover attachment means (2), cover opening (3) have been described in previous figures (FIGS. 1-7). The attachment means (2) in the current embodiment is preferably an elongated structure coupled with an edge of the cover body (1), and it may involve an adhesive, a cord/string, a belt, a hook and loop fastener (such as Velcro), an elastic band/cord, and/or a layer of foam/sponge. In certain embodiments, 2 opposite edges of the cover body (1) are associated with the attachment means (2), as shown in the present figure. In certain embodiments of the cover of the invention, adhesives (such as those commonly used in surgical drapes) may be integrated as part of the cover undersurface that comes in contact with the patient, allowing better reversible attachment of the cover to the patient.

Figure 10B:
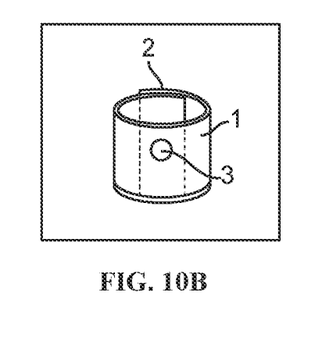

FIG. 10B illustrates the 3-dimensional view of the same embodiment of the invention illustrated in FIG. 10A, showing cover or cover body (1), cover attachment means (2), and cover opening (3). The attachment means (2) allows the cover body (1) reversibly and securely wrap around the patient undergoing the medical procedure. In the present figure, the attachment means (2) at the top edge of the cover body (1) and the attachment means (2) at the bottom edge of the cover body (1) allow the formation of a hollow lumen formed by the cover body (1), which accommodates the torso/limbs/or any body part of the patient undergoing the medical procedure. The cover opening (3) is placed in the vicinity of the target body orifice. Such method of reversibly securing the cover body (1) around the patient undergoing the medical procedure, as illustrated in the present figure, may improve the entrapment of aerosols and droplets emanating from the target body orifice during the medical procedure.

Note that any of the embodiments of the invention described earlier may be coupled with an additional suction/evacuation device of any design (such as dental oral suction device for upper GI/oral cavity procedures or a suction tubing system in the hospital rooms etc.) to further minimize health care worker exposure to aerosols and droplets generated during the medical procedure. The use of such suction/evacuation device in the vicinity of the target body orifice/cavity allows better evacuation of the aerosols and droplets generated during the endoscopic procedure. The coupling of such suction/evacuation devices with the current barrier cover invention (FIGS. 1-7) are also covered within the scope of the present invention.

Although the invention has been described in considerable detail in language specific to structural features, it is to be understood that the invention defined in the appended claims is not necessarily limited to the specific features described. Rather, the specific features are disclosed as exemplary preferred forms of implementing the claimed invention. Stated otherwise, it is to be understood that the phraseology and terminology employed herein, as well as the abstract, are for the purpose of description and should not be regarded as limiting. Therefore, while exemplary illustrative embodiments of the invention have been described, numerous variations and alternative embodiments will occur to those skilled in the art. Such variations and alternate embodiments are contemplated, and can be made without departing from the spirit and scope of the invention.

It should further be noted that throughout the entire disclosure, the labels such as left, right, front, back, top, bottom, forward, reverse, clockwise, counter clockwise, up, down, or other similar terms such as upper, lower, aft, fore, vertical, horizontal, oblique, proximal, distal, parallel, perpendicular, transverse, longitudinal, etc. have been used for convenience purposes only and are not intended to imply any particular fixed direction or orientation. Instead, they are used to reflect relative locations and/or directions/orientations between various portions of an object.

In addition, reference to "first," "second," "third," and etc. members throughout the disclosure (and in particular, claims) are not used to show a serial or numerical limitation but instead are used to distinguish or identify the various members of the group.

What is claimed is:

1. A protective device for preventing direct exposure to the aerosols and droplets containing potentially infectious bacterial and viral matter including SARS-CoV-2 associated with COVID-19 generated during a medical or veterinary endoscopic procedure involving a body cavity or orifice of a patient, the protective device comprising: a deformable planar cover structure having an exterior surface and an interior surface configured to face towards the patient, wherein the deformable planar cover structure is impermeable to aerosols, droplets, fluids and other bacterial or viral matter, wherein the deformable planar cover structure provides a barrier between a health care worker and the body cavity or orifice of the patient; a collapsible hollow tubular sleeve protruding from the deformable cover for a length, the hollow tubular sleeve forming an opening on the deformable planar cover structure, wherein the deformable planar cover structure has a material composition that is the same as that of the hollow tubular sleeve, wherein the hollow tubular sleeve with the length that allows manual compression to collapse its lumen is continuous with the deformable planar cover structure and is configured to be positioned approximately on top of the body cavity or orifice of the patient and allow passage of an endoscope between the exterior surface and the interior surface of the deformable planar cover; and, the opening configured to be reversibly adjustable from an open position to a fully closed position to surround the endoscope via a closure mechanism that is not coplanar with the deformable planar cover.

2. The protective device of claim 1, wherein the deformable planar cover structure is partially transparent.

3. The protective device of claim 1, wherein the deformable planar cover structure is reversibly secured to a table or bed supporting the patient.

4. The protective device of claim 1, wherein the deformable planar cover structure is reversibly secured to the patient's body via an adhesive, an elastic band, a fastener, a drawstring, or a cord.

5. The device of claim 1, wherein the closure mechanism is a cord, an elastic band, a zipper, a fastener, a drawstring, a sponge, or a foam.

\* \* \* \* \*